United States Patent

O'Larte

(10) Patent No.: US 9,183,602 B2
(45) Date of Patent: Nov. 10, 2015

(54) MEDICAL DEVICE INTERFACING USING A CAMERA

(75) Inventor: David O'Larte, Peculiar, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 245 days.

(21) Appl. No.: 13/167,269

(22) Filed: Jun. 23, 2011

(65) Prior Publication Data

US 2012/0330680 A1    Dec. 27, 2012

(51) Int. Cl.
*G06Q 50/00* (2012.01)
*G06Q 50/22* (2012.01)
*G06F 19/00* (2011.01)

(52) U.S. Cl.
CPC ............ *G06Q 50/22* (2013.01); *G06F 19/3487* (2013.01)

(58) Field of Classification Search
CPC .......................................... G06Q 50/22–50/24
USPC .......................................................... 705/2–3
See application file for complete search history.

(56) References Cited

U.S. PATENT DOCUMENTS

| | | | | |
|---|---|---|---|---|
| 5,712,482 | A  * | 1/1998 | Gaiser et al. | 250/363.08 |
| 6,847,933 | B1 * | 1/2005 | Hastings | 705/2 |
| 7,088,907 | B1 * | 8/2006 | Nishijima et al. | 386/248 |
| 7,894,676 | B2 * | 2/2011 | Iizuka et al. | 382/209 |
| 2001/0051881 | A1* | 12/2001 | Filler | 705/3 |
| 2002/0038226 | A1* | 3/2002 | Tyus | 705/2 |
| 2004/0081341 | A1* | 4/2004 | Cherek et al. | 382/128 |
| 2010/0211615 | A1* | 8/2010 | Kawakami et al. | 707/805 |
| 2011/0110572 | A1* | 5/2011 | Guehring et al. | 382/131 |

* cited by examiner

*Primary Examiner* — Sheetal R Paulson
(74) *Attorney, Agent, or Firm* — Shook, Hardy & Bacon L.L.P.

(57) ABSTRACT

Methods, computer systems, and computer readable media for interfacing a medical device with an electronic medical record are provided. An image of an output of the medical device is received from a camera associated with the medical device. The image is analyzed to generate a result. The result is stored in the electronic medical record.

20 Claims, 4 Drawing Sheets

MEDICAL DEVICE INTERFACING USING A CAMERA

BACKGROUND

Many medical devices in use today are unable to interface with an electronic medical record, or are very difficult or costly to interface. Hospitals are reluctant to spend the large amounts of money needed to buy replacement medical devices that are able to interface with an electronic medical record because the existing medical devices are adequate for all other purposes. Because the devices cannot interface with the electronic medical record, hospitals are forced to physically store a paper printout from the medical device, or take the labor-intensive step of scanning the printout into the electronic medical record.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention are directed to methods, computer systems, and computer storage media for use in interfacing a medical device with an electronic medical record. As mentioned above, some medical devices are unable to connect and interface with an electronic medical record. The present invention enables these devices to interface with the electronic medical record by using a camera to capture an image of an output of the medical device. The image is analyzed to generate a result which is then stored in the electronic medical record.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the present invention are directed to methods, computer systems, and computer storage media for use in interfacing a medical device with an electronic medical record (EMR). Some medical devices are unable to connect and interface with an EMR. In brief and at a high level, the present invention enables these devices to interface with the EMR by using a camera to capture an image of an output of the medical device. The image is analyzed to generate a result which is then stored in the EMR.

Accordingly, in one embodiment, the present invention is directed toward one or more computer storage media having computer-executable instructions embodied thereon that, when executed, facilitate a method of interfacing a medical device with an EMR. An image of an output of the medical device is received from a camera associated with the medical device. The image is analyzed to generate a result which is stored in the EMR.

In another embodiment, the present invention is directed toward a system to interface a medical device with an EMR. The system comprises a camera to record an image of an output of the medical device and one or more computing devices having at least one processor. The one or more computing devices comprise an image collector component that receives the image from the camera, and a determining component that determines a region of the image to be analyzed. In addition, there is an analyzer component that analyzes the region and generates a result, and a storing component that stores the result in the EMR.

In yet another embodiment, the present invention is directed toward one or more computer storage media having computer-executable instructions embodied thereon that, when executed, facilitate a method of interfacing a medical device with an EMR. An image of an output of the medical device is received from a camera associated with the medical device. A region of the image is determined to be analyzed based upon an identity of the medical device. The region is analyzed, and a result for the region is generated. Validation of the result for the region is received to provide a validated result, and the validated result is stored in the EMR.

Figure 1:
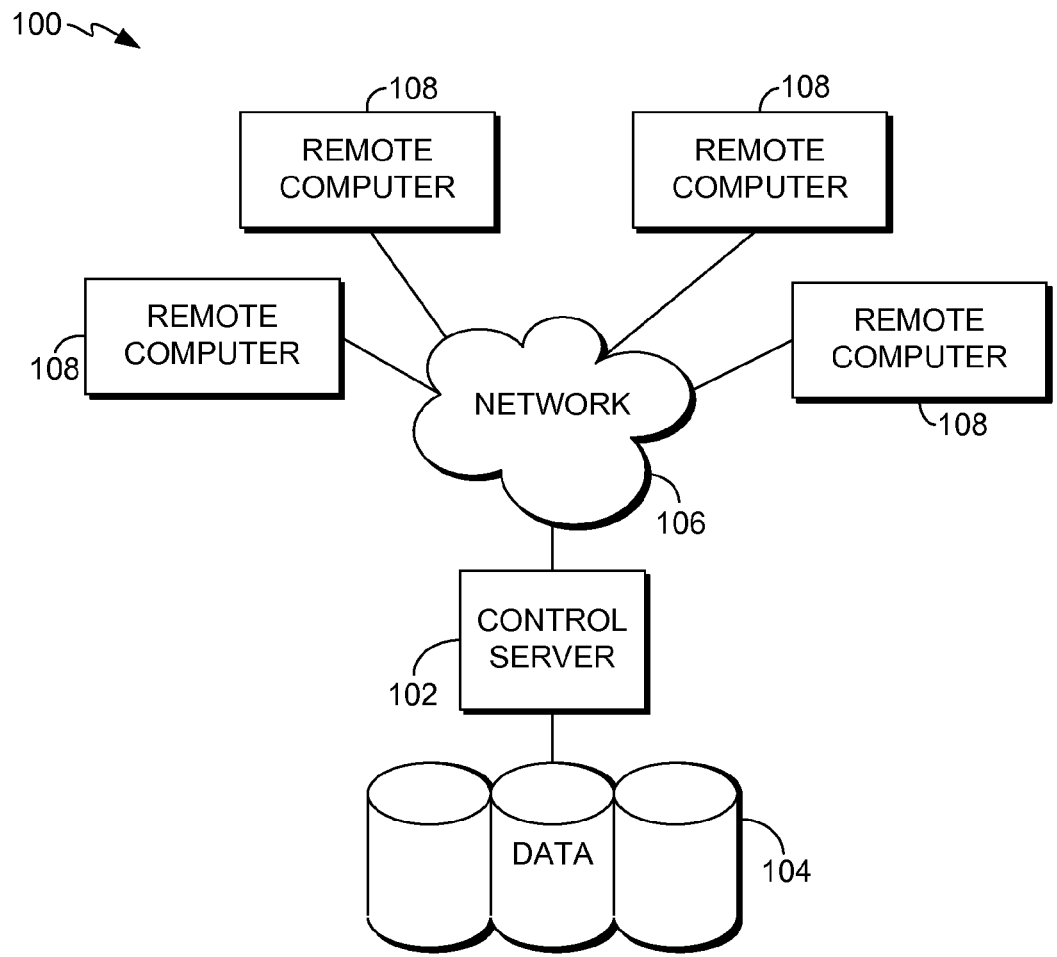
FIG. 1 is a block diagram of an exemplary computing environment suitable to implement embodiments of the present invention.

Having briefly described embodiments of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
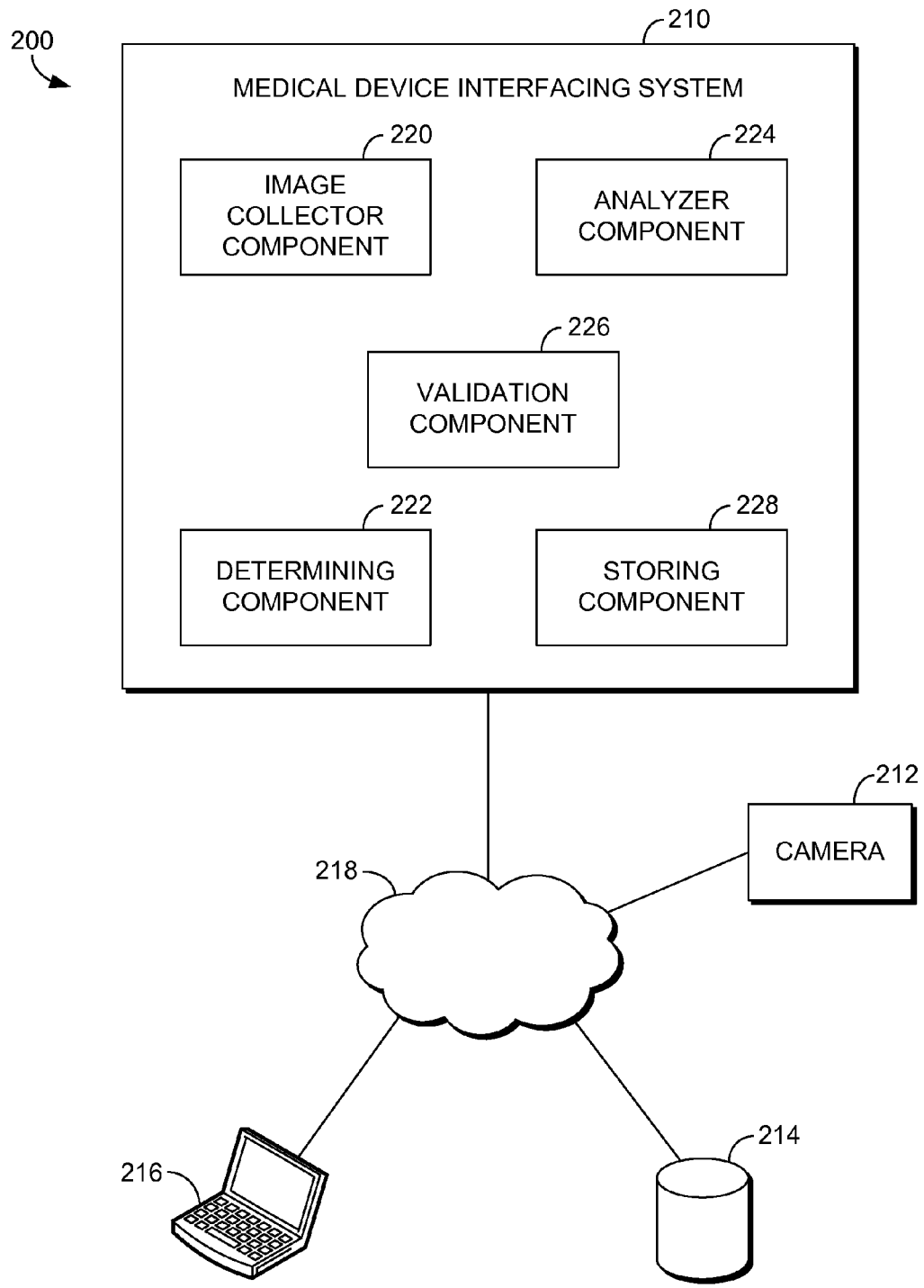
FIG. 2 is a block diagram of an exemplary system environment suitable for interfacing a medical device with an electronic medical record in accordance with an embodiment of the present invention.

Turning now to FIG. 2, an exemplary system environment suitable for interfacing a medical device with an EMR is depicted and is referenced generally by the numeral 200. It will be understood that the system environment 200 shown in FIG. 2 is merely an example of one suitable system environment for use with embodiments of the present invention. Neither should the system environment 200 be interpreted as having any dependency or requirement related to any single module/component or combination of modules/components illustrated therein. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The system environment 200 includes a medical device interfacing system 210, a camera 212, an electronic medical record (EMR) 214, an end-user computing device 216, and a network 218. Each of the components 210, 212, 214, and 216 may be in communication with each other via the network 218. The network 218 may include, without limitation, one or more local area networks (LANs) and/or wide area networks (WANs). Such networking environments are commonplace in offices, enterprise-wide computer networks, intranets and the Internet. Accordingly, the network 218 is not further described herein.

The camera 212 may comprise any camera capable of recording or capturing an image and interfacing with a computing device such as, for example, one of the remote computers 108 of FIG. 1. In one aspect, the camera 212 is a Web camera capable of directly downloading images to a computer for transmission over the network 218. In yet another aspect, the Web camera is wireless.

The camera 212 may be associated with a patient and/or a medical device. The association may occur in several different ways. For example, the camera 212 may have software that enables the camera 212 to be associated with a medical device which, in turn, is associated with a patient. In some embodiments, the camera 212 may be physically attached to a medical device. Therefore, if it is known that the medical device is associated with a patient by, for example, associating a product identification of the medical device with a patient identification, then it can be assumed that the camera 212 is associated with the patient because it is physically attached to the medical device. This association may be strengthened by positioning the camera 212 that is attached to the medical device so that it captures or records the product identification of the medical device. For example, the camera 212 may be positioned so that it captures a serial number of the medical device, or a bar code of the medical device. The recorded product identification of the medical device can be used as a check to verify the camera-to-patient association.

In another embodiment, a clinician may manually associate the camera 212 with a medical device and a patient by manually entering association information into, for example, the medical device interfacing system 210. For instance, the clinician may be interested in obtaining a one-time measurement of blood oxygen levels of a patient using a pulse oximeter. The clinician manually associates the camera 212 and the pulse oximeter device with the patient and obtains an image; the clinician then manually disassociates the camera 212 and the pulse oximeter device from the patient. The image obtained in this manner is known to be associated with the pulse oximeter device and the patient.

In one embodiment of the invention, the camera 212 may be positioned so that its field of view captures the entire output of a medical device. The entire output may subsequently be analyzed to generate a series of results. Alternatively, selected regions of the output may be analyzed to generate results. In another embodiment, the camera 212 may be positioned so that its field of view captures a discrete region of the image. The region, when subsequently analyzed, may generate one result.

The EMR 214 may comprise electronic clinical documents such as images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. The electronic clinical documents must be authenticated or signed to be considered a valid, legal medical record. Authenticated medical records stored in the EMR 214 are searchable and accessible for use in patient care. However, the EMR 214 may also store unvalidated data and/or images. The unvalidated data and/or images may still be used by clinicians in the decision-making process The end-user computing device 216 may be any type of computing device such as, for example, any of the remote computers 108 of FIG. 1. The end-user computing device 216 may include a display screen (not shown). The display screen is configured to display information to the user of the end-user computing device 216, for instance, information relevant to communications initiated by and/or received by the end-user computing device 216, images, results, and the like. Embodiments are not intended to be limited to visual display but rather may also include audio presentation, combined audio/visual presentation, and the like.

The medical device interfacing system 210 shown in FIG. 2 may be any type of computing device such as, for example, any of the remote computers 108 or the control server 102 of FIG. 1. By way of example only and not limitation, the medical device interfacing system 210 may be a personal computer, desktop computer, laptop computer, handheld device, mobile handset, consumer electronic device, server device, or the like. It should be noted, however, that embodiments are not limited to implementation on such computing devices, but may be implemented on any of a variety of different types of computing devices within the scope of embodiments hereof.

Components of the medical device interfacing system 210 may include, without limitation, a processing unit, internal system memory, and a suitable system bus for coupling various system components, including one or more data stores for storing information (e.g., files and metadata associated therewith). The medical device interfacing system 210 typically includes, or has access to, a variety of computer-readable media.

While the medical device interfacing system 210 is illustrated as a single unit, it will be appreciated that the medical device interfacing system 210 is scalable. For example, the medical device interfacing system 210 may in actuality include a plurality of computing devices in communication with one another. Moreover, the EMR 214, or portions thereof, may be included within, for instance, the medical device interfacing system 210 as a computer-storage medium. The single unit depictions are meant for clarity, not to limit the scope of embodiments in any form.

As shown in FIG. 2, the medical device interfacing system 210 comprises an image collector component 220, a determining component 222, an analyzer component 224, a validation component 226, and a storing component 228. In some embodiments, one or more of the components 220, 222, 224, 226, and 228 may be implemented as stand-alone applications. In other embodiments, one or more of the components 220, 222, 224, 226, and 228 may be integrated directly into the operating system of, for example, any of the remote computers 108 or the control server 102 of FIG. 1 or the end-user computing device 216 of FIG. 2. The components 220, 222, 224, 226, and 228 illustrated in FIG. 2 are exemplary in nature and in number and should not be construed as limiting. Any number of components may be employed to achieve the desired functionality within the scope of embodiments hereof.

In one embodiment of the invention, the image collector component 220 is configured to receive an image from the camera 212, where the camera 212 has recorded the image from an output of a medical device. The output of the medical device may be in the form of a visual display of a video or a static image, or a printout from the medical device. As well, the output may comprise alphanumeric characters or a wave form(s) and may include the entire output of the medical device or only a portion of the output of the medical device. In another embodiment of the invention, the image collector component 220 may be configured to receive an image from a foreign or third-party system (via some type of electronic health information transmission protocol such as, for example, HL7). For example, wave form data may be received by the image collector component 220 from a foreign system via HL7 protocol. Any and all such variations are within the scope of embodiments of the present invention.

The image collector component 220 may, in one embodiment, be configured to determine an identity of a medical device the camera 212 is associated with. This can be done for example, by determining an Internet Protocol (IP) address of the camera 212. The image collector component 220 can then access a data store (for example, the data store 104 of FIG. 1) to determine which medical device is associated with the IP address of the camera 212. The data store may also contain information regarding which patient the medical device is associated with. By utilizing these pieces of data, a camera-to-medical device-to-patient association can be established. In another embodiment of the invention, the identity of the medical device associated with the camera 212 may already be known. For example, the camera 212 may always be associated with a certain medical device. Thus, any image received from the camera 212 will automatically be associated with that medical device. In another embodiment, the identity of a medical device associated with the camera 212 may already be known because a clinician manually associated the medical device and the camera 212 with a patient as outlined above. Still further, in yet another embodiment, when an image is received from a foreign system, the identity of the medical device that generated the image may be associated with the image.

In some embodiments, the image collector component 220 may be configured to temporarily store the image upon receiving the image and prior to analyzing the image. Images stored in this manner may still be accessible by clinicians for decision-making purposes. For example, the image collector component 220 may temporarily store the image in the EMR 214 or in an intermediate data store. Still further, the image may be temporarily stored based on an identity of the medical device. The identity of the medical device may include the type of medical device, (i.e., a vital signs monitor), the company that produced the medical device, the model or serial number of the medical device, and the like. In yet another aspect, the image may be stored in a work queue that is prioritized based on the identity of the medical device. For example, images received from vital signs monitors may have a higher priority in the work queue than images from an optical instrument used for everyday eye exams. Images may also be prioritized based on a clinical status of a patient (stable, critical, etc.), a clinician identity, time till discharge, and the like.

In some embodiments of the invention, the image collector component 220 may be configured to cause the camera 212 to record images. The image collector component 220 may cause the camera 212 to record images at fixed intervals or upon determining that an image has changed in some material way beyond just background noise. For example, it may be determined that a threshold number of pixels that comprise the image have changed.

The determining component 222 is configured for determining a region of the image to be analyzed. This determination is dependent upon the identity of the medical device as determined by, for example, the image collector component 220. In one embodiment, the determining component 222 may determine that the entire image, and not just a region of the image, should be analyzed. For instance, the entire output of an electrocardiogram (EKG) monitor contains useful information. The determining component 222 determines that an entire image of the output should be analyzed based on the identity of the medical device—an EKG monitor.

In another embodiment, the determining component 222 may determine that a region of the image needs to be analyzed. For example, some regions of the image contain data that is not particularly useful for helping clinicians make decisions regarding patient care. But other regions of the image contain useful data. Again, the identity of the medical device determines which regions of the image have useful data that should be analyzed. By way of illustrative example, a spirometer measures the volume of air inspired and expired by the lungs. The output of the spirometer may be a printout with a wave form where the peak of the wave form indicates maximum exhalation and the trough of the wave form indicates maximum inspiration. A clinician would be interested in data regarding the peaks and troughs but not necessarily data associated with other parts of the wave form.

The analyzer component 224 is configured to analyze an image and/or determined region and generate results. One result may be generated or multiple results may be generated. Images and/or regions containing alphanumeric text may be analyzed using optical character recognition (OCR) technology, while images and/or regions that consist of wave forms may be analyzed by using waveform analysis including Fourier analysis. The results may include numerical values or text.

In one embodiment, when a medical device is always associated with the camera 212 or when a clinician manually associates a medical device with the camera 212, the analyzer component 224 analyzes the image and generates results without, for example, the image collector component 220 determining an identity of the medical device. In another embodiment, the analyzer component 224 analyzes the image and generates results based on knowledge of the identity of the device as determined by, for example, the image collector component 220. In yet another embodiment, the analyzer component 224 analyzes a region of the image and generates results, where the region analyzed is determined by, for example, the determining component 222 based on an identity of the medical device.

In one aspect of the invention, a tagging component (not shown) is configured to tag the image or a region of the image with a result(s). Thus, a clinician viewing the image would see tags corresponding to the result(s). In the example given above regarding the spirometer, a clinician could access the spirometer readout image from, for example, the EMR 214 and view the image. The peaks of the image would be tagged with a FEV1 value, and the troughs of the image would be tagged with a FIV1 value.

In yet another aspect of the invention, the validation component 226 is configured to present the image, and/or region, and the result(s) to a user and receive validation from the user indicating that the result(s) is valid for the image and/or region. The validation component 226 may also be configured to present an image with a tagged region to a user and receive validation of the tagged region from the user indicating that the tagged region is valid for the image. The user may be a clinician involved in the patient's care. Or the user may be an "image transcriptionist." If the image does not contain sensitive patient information, it is possible for the transcription process to be performed outside of patient/provider confidentiality guidelines. Once the clinician and/or the image transcriptionist has verified that the result is valid for the image and/or region, or that the tagged region is valid for the image, the image can be signed. Once the image is signed or authenticated it is considered a valid, signed medical record that can be accessed from the EMR 214 and used to care for the patient.

The storing component 228 is configured to store the result(s) in, for example, the EMR 214. In one aspect, the storing component 228 is configured to store the result(s) and/or the image in the EMR 214. In yet another aspect, the storing component 228 is configured to store the image and/or any tagged regions in the EMR 214. In one embodiment, the storing component 228 may be configured to identify a proper location in the EMR 214 for storing the result(s). The location may be dependent upon what type of medical device generated the result(s).

The storing component 228 may store the result(s), and/or the image, and/or the tagged region in the EMR 214 before receiving validation or after receiving validation. If it is stored before validation, a clinician or image transcriptionist would still be able to access the image or results from the EMR 214 by using, for example, a patient identification and use the image or results for decision-making purposes. The result may then be validated and re-stored in the EMR 214. If it is stored after receiving validation, it is considered a valid, signed medical record. At this point, the image can be searched and accessed by a clinician and used to guide decisions regarding patient care.

Figure 3:
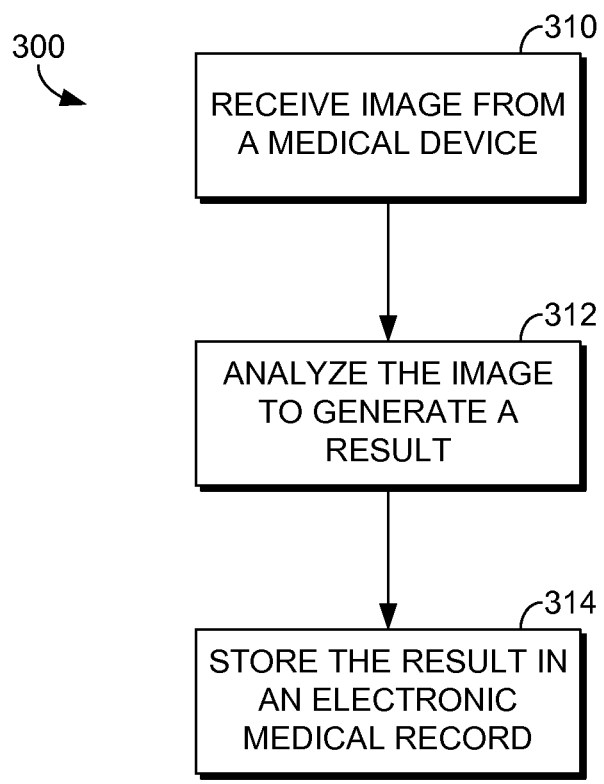
FIG. 3 depicts a flow diagram illustrating a method for interfacing a medical device with an electronic medical record suitable to implement embodiments of the present invention.

Turning now to FIG. 3, a high-level flow diagram is depicted illustrating a method for interfacing a medical device with an electronic medical record and is referenced generally by the numeral 300. At step 310, an image of an output of a medical device is received by, for example, the image collector component 220 of FIG. 2. The image may be received from a camera associated with the medical device. More specifically, the image may be received from a wireless Web camera associated with the medical device. The association between the camera and the medical device may be created manually by a clinician, or the association may occur by physically attaching the camera to the medical device and positioning it so that it captures a product identification of the medical device. The image may be of the entire output of the medical device, or, alternatively, the image may be of a portion of the output of the medical device. In turn, the image may be received at fixed intervals, or the image may only be received if it is determined that the image has changed in some material way. In another embodiment of the invention, an image may be received from a foreign or third-party system.

At step 312, the image is analyzed to generate a result. In one embodiment, the entire image is analyzed to generate one or more results. In another embodiment, an identity of the medical device associated with the camera is determined before the image is analyzed. This may be done by, for example, the image collector component 220 of FIG. 2. In yet another embodiment, a region of the image is determined to be analyzed to generate one or more results by, for example, the determining component 222 of FIG. 2. The region to be analyzed may be dependent upon an identity of the medical device that generated the image. At step 314, the result(s) is stored in the EMR (for example, the EMR 214 of FIG. 2) by, for example, the storing component 228 of FIG. 2. In one embodiment, the entire image along with the result is stored in the EMR. In another embodiment, just the result is stored in the EMR.

Figure 4:
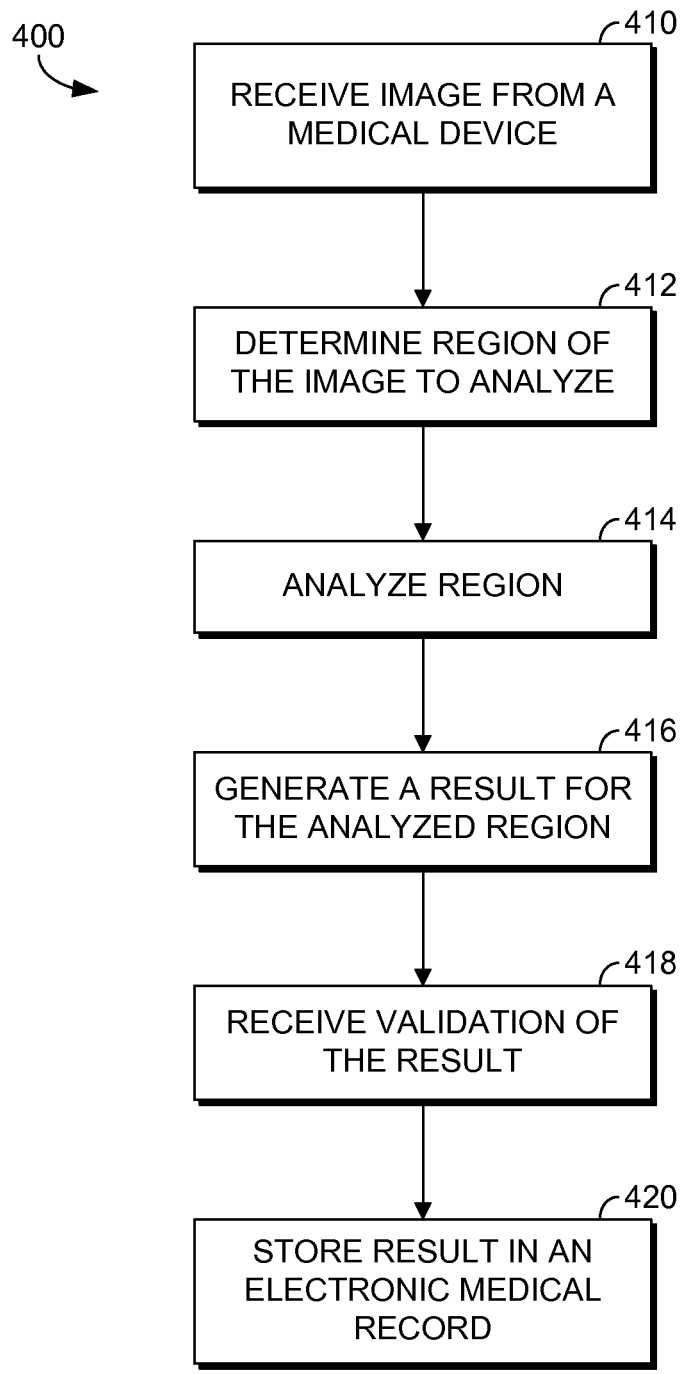
FIG. 4 depicts a flow diagram illustrating a method for interfacing a medical device with an electronic medical record suitable to implement embodiments of the present invention.

Turning now to FIG. 4, a more detail-oriented flow diagram is depicted illustrating a method for interfacing a medical device with an electronic medical record and is referenced generally by the numeral 400. At step 410, an image of an output of a medical device is received from, for example, a camera such as the camera 212 of FIG. 2. The camera may be a wireless Web camera. The camera may capture images at fixed intervals or upon determining that the image has changed in some material way. The image may be of the entire output of the medical device or a portion of the output. In one embodiment, the image may be temporarily stored in a work queue upon receipt. The work queue may be stored in the EMR based upon an identity of the medical device that produced the image, and images in the work queue may be prioritized based on the identity of the medical device, a clinical status of the patient from which the image was obtained, a clinician identity, and the like. Images that are temporarily stored in the work queue may be available to clinicians for decision-making purposes.

Continuing with respect to step 410, an image may be received from a foreign or third-party system via some type of electronic health information transmission protocol. Images received in this manner may include information detailing an identity of a medical device that produced the image.

At step 412, a region of the image is determined to be analyzed based upon an identity of the medical device. This determination may be made by, for example, the determining component 222 of FIG. 2. As mentioned above, the identity of the medical device may include a type of the medical device, a manufacturer of the medical device, a serial number of the medical device, and the like. In one embodiment, it may be determined that the entire image should be analyzed based on the identity of the medical device. In another embodiment, it may be determined that only a region of the image contains useful information based on the identity of the medical device, and only that region is determined to be analyzed.

At step 414, the region of the image is analyzed. Optical character recognition may be used if the region contains alphanumeric characters, and waveform analysis may be used if the region includes wave forms. At step 416, a result is generated for the analyzed region. The result may be a numerical value or text. In one embodiment, the image and/or region is tagged with the result.

At step 418, validation of the result is received to provide a validated result. Validation may be received after presenting the image and/or region and the result to a user and receiving validation from the user indicating that the result is valid for the image and/or region. The user may be a clinician involved in patient care, or, if privacy concerns are maintained, the user may be an image transcriptionist that validates the image outside of the normal healthcare setting. If the image and/or region has been tagged with the result, the tagged image and/or region may be validated.

At step 420, the validated result is stored in an EMR such as the EMR 214 of FIG. 2. In one embodiment, the result may be stored in a location that is dependent upon the identity of the medical device that produced the image.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more computer storage media having computer-executable instructions embodied thereon that, when executed, facilitate a method of enabling a medical device to interface with an electronic medical record, wherein the medical device is unable to connect directly to and interface directly with the electronic medical record, the method comprising:
    creating an electronic association between a camera and the medical device, wherein the medical device has been electronically associated with a patient, wherein the medical device is used to monitor a medical condition of the patient and to generate an output related to the monitored medical condition of the patient, and wherein the camera is positioned to capture an image of the output generated by the medical device;
    receiving, from the camera, the image of the output generated by the medical device;
    based on an identity of the medical device, determining a region of the image of the output generated by the medical device includes data relevant to the monitored medical condition of the patient;
    automatically and without human intervention analyzing the region of the image of the output generated by the medical device to generate at least one result associated with the monitored medical condition of the patient; and
    storing the at least one result in the electronic medical record for the patient.

2. The one or more computer storage media of claim 1, wherein the method further comprises:
    causing the camera to record the image.

3. The one or more computer storage media of claim 2, wherein the camera comprises a Web camera.

4. The one or more computer storage media of claim 2, wherein the causing the camera to record the image occurs upon determining that the image has changed in a material way.

5. The one or more computer storage media of claim 2, wherein the camera is electronically associated with the patient.

6. The one or more computer storage media of claim 2, wherein the output of the medical device includes a visual display or a printout.

7. The one or more computer storage media of claim 2, wherein the output of the medical device comprises alphanumeric characters or a wave form.

8. The one or more computer storage media of claim 7, wherein the alphanumeric characters are analyzed using optical character recognition and the wave form is analyzed using waveform analysis.

9. The one or more computer storage media of claim 2, wherein the at least one result comprises at least one numerical value or text.

10. The one or more computer storage media of claim 2, wherein the method further comprises:
    presenting the image and the at least one result to a user; and
    receiving validation from the user indicating that the at least one result is valid for the image.

11. The one or more computer storage media of claim 2, wherein the method further comprises:
    tagging the region with the at least one result.

12. The one or more computer storage media of claim 11, wherein the method further comprises:
    presenting the image with the tagged region to a user;
    receiving validation of the tagged region from the user indicating that the tagged region is valid for the image; and
    storing the tagged region in the electronic medical record.

13. The one or more computer storage media of claim 2, wherein the method further comprises:
    storing the image in the electronic medical record.

14. A system that enables a medical device to interface with an electronic medical record, wherein the medical device is unable to connect directly to and interface directly with the electronic medical record, the system comprising:
    a camera that is positioned to record an image of an output generated by the medical device, wherein the output generated by the medical device relates to a monitored medical condition of a patient, wherein the camera has been electronically associated with the medical device, and wherein the medical device has been electronically associated with the patient; and
    one or more computing devices having at least one processor and comprising:
        (1) an image collector component that receives, from the camera, the image of the output generated by the medical device,
        (2) a determining component that determines a region of the image of the output generated by the medical device to be analyzed based upon an identity of the medical device, wherein the region is determined to include data relevant to the monitored medical condition of the patient based on the identity of the medical device,
        (3) an analyzer component that automatically and without human intervention analyzes the region and generates at least one result associated with the monitored medical condition of the patient, and
        (4) a storing component that stores the at least one result in the electronic medical record.

15. The system of claim 14, wherein the camera is physically attached to the medical device.

16. The system of claim 15, wherein the camera is further positioned to record a product identification of the medical device.

17. The system of claim 14, further comprising:
    a validation component that receives validation of the at least one result.

18. One or more computer storage media having computer-executable instructions embodied thereon that, when executed, facilitate a method of enabling a medical device to interface with an electronic medical record, wherein the medical device is unable to connect directly to and interface directly with the electronic medical record, the method comprising:
    creating an electronic association between a camera and the medical device, wherein the medical device has been electronically associated with a patient, and wherein the medical device is used to monitor a medical condition of the patient and to generate an output related to the monitored medical condition of the patient;
    receiving an image of the output of the medical device from the camera, wherein the camera is positioned to capture the image of the output generated by the medical device;

based on an identity of the medical device, the identity including a medical device type, determining a region of the image of the output of the medical device includes data relevant to the monitored medical condition of the patient;

automatically and without human intervention analyzing the region of the image of the output of the medical device;

generating a result for the region, wherein the result is associated with the monitored medical condition of the patient;

receiving user validation of the result for the region to provide a validated result; and storing the validated result in the electronic medical record for the patient.

19. The one or more computer storage media of claim 18, wherein the validated result is a valid medical record.

20. The one or more computer storage media of claim 1, wherein the method further comprises:

storing the image in a work queue for a user; and based on the identity of the medical device, assigning a work queue priority to the image.

* * * * *